United States Patent
Hughes et al.

(10) Patent No.: US 11,883,525 B2
(45) Date of Patent: Jan. 30, 2024

(54) BIOERODIBLE POLYESTER POLYMER AXITINIB OCULAR IMPLANTS AND RELATED METHODS OF USE

(71) Applicant: Dose Medical Corporation, San Clemente, CA (US)

(72) Inventors: Patrick Michael Hughes, San Clemente, CA (US); James Shiah, San Clemente, CA (US); Jack Xie, San Clemente, CA (US); Jia-Ying Yang, San Clemente, CA (US)

(73) Assignee: DOSE MEDICAL CORPORATION, San Clemente, CA (US)

( * ) Notice: Subject to any disclaimer, the term of this patent is extended or adjusted under 35 U.S.C. 154(b) by 102 days.

(21) Appl. No.: 16/888,384

(22) Filed: May 29, 2020

(65) Prior Publication Data

US 2020/0375889 A1    Dec. 3, 2020

Related U.S. Application Data

(60) Provisional application No. 62/855,666, filed on May 31, 2019.

(51) Int. Cl.
*A61K 9/00*    (2006.01)
*A61K 47/34*   (2017.01)
*A61K 31/4439* (2006.01)

(52) U.S. Cl.
CPC .......... *A61K 9/0019* (2013.01); *A61K 9/0051* (2013.01); *A61K 31/4439* (2013.01); *A61K 47/34* (2013.01)

(58) Field of Classification Search
CPC ..................... A61K 9/0019; A61F 2210/0004
See application file for complete search history.

(56) References Cited

U.S. PATENT DOCUMENTS

| 8,512,738 B2 | 8/2013 | Edelman et al. |
| 8,685,435 B2 * | 4/2014 | Nivaggioli ........... A61K 9/0051 424/427 |
| 2005/0244470 A1 | 11/2005 | Hughes et al. |

(Continued)

FOREIGN PATENT DOCUMENTS

| AU | 2011211380 B9 | 5/2014 |
| WO | 2018209155 A1 | 11/2018 |

OTHER PUBLICATIONS

Giddabasappa et al (Experimental Eye Research, vol. 145, pp. 373-379) (Year: 2016).*

(Continued)

*Primary Examiner* — Carlos A Azpuru
(74) *Attorney, Agent, or Firm* — Stoel Rives LLP

(57) ABSTRACT

The present disclosure provides compositions that enable sustained release of a small molecule tyrosine kinase inhibitor, such as axitinib from a bioerodible polyester polymer implant for the treatment of disease. The composition is especially suitable for treating ophthalmic indications, such as neovascular age related macular degeneration and diabetic macular edema, by intravitreal injection of the implant. The implant is designed to be pre-loaded into a small diameter needle and injected via self-sealing scleral needle penetration at the pars plana. Small molecule tyrosine kinase inhibitors may be released from the implants over a period of one week to three years.

13 Claims, 12 Drawing Sheets

(56) References Cited

U.S. PATENT DOCUMENTS

| | | |
|---|---|---|
| 2016/0213662 A1 | 7/2016 | Zarnitsyn et al. |
| 2017/0173161 A1 | 6/2017 | Kaplan et al. |
| 2018/0228649 A1 | 8/2018 | Lerner |
| 2018/0256497 A1* | 9/2018 | Popov .................. A61K 9/5031 |
| 2018/0311260 A1 | 11/2018 | Bodick et al. |

OTHER PUBLICATIONS

International Search Report and Written Opinion dated Aug. 28, 2020 for international application PCT/US2020/035379.

* cited by examiner

| # | 202S | 203S | 502 | 503 | 752H | 756S | Axitinib (40 and 60%) | Total (mg) |
|---|---|---|---|---|---|---|---|---|
| 1 | 80 | | | | | | 120 | 200 |
| 2 | | 80 | | | | | 120 | 200 |
| 3 | | | 80 | | | | 120 | 200 |
| 4 | | | | 80 | | | 120 | 200 |
| 5 | | | | | 80 | | 120 | 200 |
| 6 | | | | | | 80 | 120 | 200 |
| 7 | | 40 | | | | 40 | 120 | 200 |
| 8 | 40 | | | | | 40 | 120 | 200 |
| 9 | | 40 | 40 | | | | 120 | 200 |
| 10 | | 40 | | 40 | | | 120 | 200 |
| Total (mg) | 120 | 200 | 80 | 120 | 120 | 160 | 1200 | 2000 |

*FIG. 1B*

BIOERODIBLE POLYESTER POLYMER AXITINIB OCULAR IMPLANTS AND RELATED METHODS OF USE

RELATED APPLICATIONS

This application claims priority to U.S. Provisional Patent Application No. 62/855,666, filed May 31, 2019, and titled BIOERODIBLE POLYESTER POLYMER IMPLANTS AND RELATED METHODS OF USE, which is incorporated herein by reference in its entirety.

TECHNICAL FIELD

The present disclosure relates to implants for treating ocular diseases, such as neovascular age-related macular degeneration (nAMD) and diabetic macular edema (DME), by intravitreal injection of the implant. More specifically, the implant includes a composition that enables the sustained release of a small molecule tyrosine kinase inhibitor (TKI), such as axitinib, from a bioerodible polyester polymer implant for the treatment of disease.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1B is a table of formulation design matrix of PLA, PLGA and blends.

DETAILED DESCRIPTION

Figure 1A:
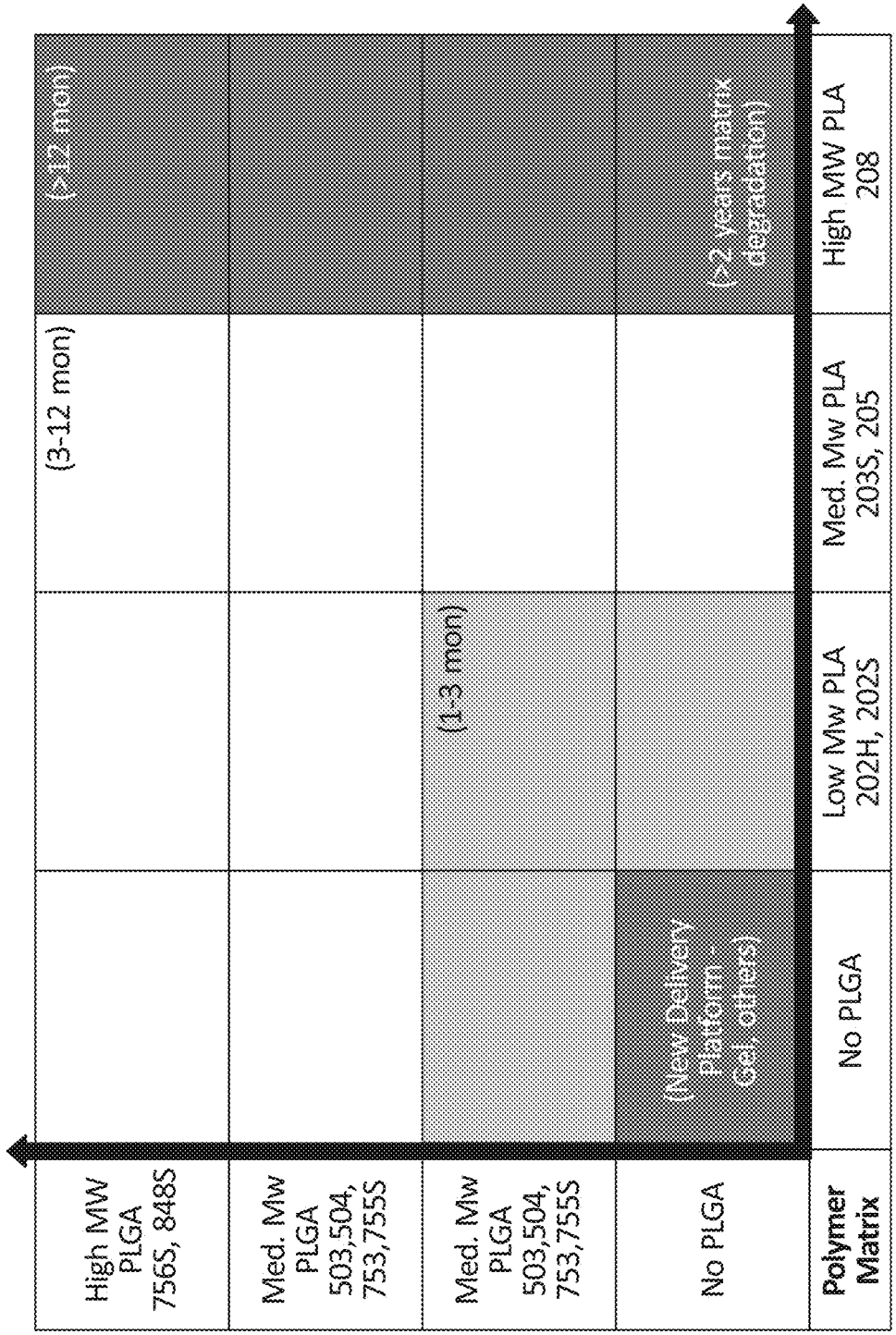
FIG. 1A is a chart exemplifying the effect of different co-monomer ratios or molecular weights (MW) of PLGA or PLA on drug release and polymer matrix degradation for implant formulations.

From a drug delivery standpoint, the eye can be separated into anterior and posterior segments. The anterior segment includes the lids, conjunctiva, cornea, aqueous humors, trabecular meshwork, iris, ciliary body and lens. The posterior segment is made up of the uveal tract, vitreous humor, retina, retinal pigmented epithelium, and choroid.

Diseases of the anterior segment include conjunctivitis, dry eye and ocular hypertension. Numerous disease states also affect the posterior segment of the eye and cause significant morbidity. These include neovascular age-related macular degeneration (nAMD), uveitis, proliferative vitreal retinopathy, diabetic macular edema (DME), and retinal vein occlusion, amongst others. New pharmacologic agents are being developed that can be used to treat these diseases; however, they must achieve therapeutic concentrations in the affected tissues to be effective. Hence, for diseases of the vitreous, retina, choroid and uveal tract, a drug must reach the posterior segment.

The eye poses considerable challenges for both topical and systemic delivery of drugs to the posterior segment. Topical delivery to the anterior segment of the eye is highly inefficient with typical bioavailability of between 1% to 5%. Further movement from the anterior chamber to the posterior segment is prevented by the iridolenticular diaphragm. What little drug that enters the anterior-most portions of the posterior segment from topical delivery must also overcome a large diffusional barrier to reach the macula area of the eye. These hurdles render topical administration of drugs to the posterior segment mostly ineffective. In addition, the blood retinal barrier greatly minimizes or prevents systemic delivery to the posterior segment. Due to these constraints, most drugs used to treat posterior segment ophthalmic diseases are administered by intravitreal administration.

Due to the barriers to absorption to the posterior segment of the eye and the rapid vitreal clearance of most small molecules (<10 hours), the most effective route of drug administration is by multiple intravitreal injections. Direct intravitreal injection is currently the route of administration for most retina drugs including Kenalog-40®, Triesence®, Eylea®, Avastin® and Lucentis® (ranibizumab injection). Multiple intraocular injections are required to maintain the therapeutic effect from these solution and suspension dosage forms. This carries the risk of poor patient compliance, intravitreal hemorrhages, retinal and vitreous detachment, cataract, and endophthalmitis. Sustained and controlled delivery directly into the vitreous addresses this problem and also tempers the potential high peak drug levels achieved through frequent pulsed dosing. For this reason, there is a very significant unmet medical need for sustained intraocular drug delivery systems.

Vascular endothelial growth factor (VEGF) has been implicated in retinal neovascularization, and inhibiting VEGF to treat exudative ophthalmic diseases is clinically validated. Currently, bevacizumab (Avastin®), ranibizumab (Lucentis®) and aflibercept (Eylea®) are clinically effective in treating nAMD and DME. These are macromolecular ligands for VEGF and work extracellularly. Small molecule tyrosine kinase inhibitors (TKIs) also inhibit VEGF, but act on intracellular targets. Hence, these molecules need to have the appropriate disposition to and into the target cells from their route of administration. Many of these compounds have achieved significant clinical success in treating cancer. Axitinib (Inlyta®, Pfizer) is approved for the treatment of renal cell carcinoma with daily doses ranging up to 20 mg. Additionally, systemic administration of axitinib to rats by an infusion pump inhibited vascular leakage in a laser-induced rat choroidal neovascularization model. However, direct intraocular administration would be required to treat retinal diseases to prevent systemic side effects from a small molecule tyrosine kinase inhibitor.

Treatment of nAMD or DME with small molecule tyrosine kinase inhibitors (TKIs) has not met with success so far. Several preclinical studies and clinical studies have assessed TKIs for the treatment of retinal vascular leakage by many routes of administration: topical drops, systemic administration, intravitreal injection of suspensions and intravitreal injection of polymeric TKI microparticles. Topical administration of small molecule TKIs has not been shown to achieve clinically significant concentrations of the TKI at the macula. Additionally, significant non-productive absorption into the systemic circulation occurs with topical dosing leading to significant potential side effects. Systemic dosing of TKIs also carries the significant potential for off-target effects and severe adverse events. It has been shown that most particulate dosage forms, suspensions or sustained release microparticles are not well tolerated in the back of the eye causing retinal inflammation, traction retinal detachment, adherence of the particulates to the lens and migration of the particles into the anterior chamber. The exception to this are steroids, such as triamcinolone acetonide.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The present disclosure provides compositions that enable the sustained release of a small molecule TKI, such as axitinib, from a bioerodible polyester polymer implant for the treatment of disease. The composition is especially suitable for treating ophthalmic indications such as nAMD and DME by intravitreal injection of the implant. The implant is designed to be pre-loaded into a small-gauge needle and injected via self-sealing scleral needle penetration at the pars plana. Small molecule TKI, such as axitinib, may be released from the implant in vitro or in vivo over a period of one week to three years.

The present disclosure also provides an intravitreal implant that is configured to be delivered to or implanted into an eye of a subject or a patient. The intravitreal implant may release a therapeutic agent into a vitreous humor of the eye of the subject at an effective rate for at least six months. The intravitreal implant may release the therapeutic agent and may release the therapeutic agent for at least one year from implantation.

The implant may include a bioerodible polyester polymer blend and a therapeutic agent. The therapeutic agent may be a small molecule tyrosine kinase inhibitor (TKI). The TKI may be selected from at least one of axitinib, dasatinib, erlotinib, imatinib, nilotinib, pazopanib, sunitinib, tivozanib, lentvatinib, and the like. The effective rate of release of the TKI may range from about 10 ng/day to about 10 mg/day.

In some embodiments, after implantation, there may be an initial burst release phase during which time the therapeutic agent is released from the polymer at a rate faster than the substantially constant rate it subsequently maintains for a period of time. The burst release phase can vary in length between a few minutes and several days depending on the therapeutic agent and the polymer matrix. In some embodiments, the burst release of therapeutic agent from the composite implant may be less than about 10% (w/w) during the burst release phase. In certain embodiments, the burst release of therapeutic agent from the composite implant may be less than about 9% (w/w), less than about 8% (w/w), less than about 7% (w/w), less than about 6% (w/w), less than about 5% (w/w), less than about 4% (w/w), less than about 3% (w/w), less than about 2% (w/w), or less than about 1% (w/w) during the burst release phase. In other embodiments, the burst release of therapeutic agent from the composite implant may be less than about 1% (w/w) during the burst release phase. For example, in some embodiments, the burst release of the therapeutic agent form the composite implant may be less than about 10% (w/w) over an initial 24-hour period from implantation in an eye of a patient. In other embodiments, the burst release of the therapeutic agent form the composite implant may be less than about 1% (w/w) over an initial 24-hour period from implantation in an eye of a patient. The phrases "from implantation" and "after implementation" may be used interchangeably.

The release rate of the therapeutic agent from the implant may be substantially constant. In some embodiments, the release rate of the TKI from the implant is substantially constant over an initial three-month period from implantation beginning with the end of the burst release or lag phase, but not more than approximately 14 days post-implantation or initiation of in vitro release studies. In some embodiments, the release rate of the TKI from the implant is substantially constant over an initial three-month period from implantation beginning with the end of the burst release or lag phase, but not more than approximately 28 days post-implantation or initiation of in vitro release studies. The lag phase is defined as the period immediately post-implantation or immediately after initiating in vitro release studies where no drug is released or the drug is released at a slower rate than the constant rate achieved after not more than 14 days.

The release rate of the therapeutic agent from the implant may be near-zero order or pseudo-zero order over some period of time. In certain embodiments, the release rate of the TKI from the implant is near-zero order or pseudo-zero order over an initial three-month period from implantation beginning with the end of the burst release or lag phase, but not more than 14 days post-implantation or initiation of in vitro release studies. Near-zero order release and pseudo-zero order release kinetics are defined as an essentially linear relationship of the cumulative amount of therapeutic agent released from the implant in vivo or in in vitro release studies as a function of time.

The bioerodible polyester polymer blend may comprise a plurality of different polyester polymers. Exemplary polyester polymers may include poly(glycolic acid) (PGA), poly(lactic acid) (PLA), and the copolymer poly(lactic-co-glycolic acid) (PLGA). These polymers have been used with considerable success in the clinic as suture materials, as orthopedic fixation devices, and for drug delivery. Some examples of approved and commercialized drug delivery systems comprising PLA/PLGA polymers include: Nutropin® Depot (human growth hormone), Sandostatin LAR® (octreotide), Trelstar® Depot (triptorelin pamoate), and Zoladex® (goserelin acetate).

Therapeutic agent delivery systems comprised of PLA/PLGA can be manufactured by various means as microparticles with therapeutic agents dispersed within, extruded as polymeric implants from a drug polymer blend, formed into core/shell implants with the PLA/PLGA as an outer shell or coating and an inner drug matrix core, formed into tablets, wafers or implants by compression molding of drug polymer blends and other morphologies and dosage forms. A therapeutic agent may be released from a PLA/PLGA drug matrix by means of diffusion from the polymer delivery system. This proceeds by hydration of the implant along with concurrent erosion of the polymer chains and diffusion of the drug out of the system.

The rate of the therapeutic agent release and polymer erosion is controlled by many factors including therapeutic agent solubility, particle size, domain size, lipophilicity and crystallinity as well as polymer co-monomer ratio, crystallinity, molecular weight (MW), end group (ester or acid), residual monomers and solvents, manufacturing processes, and porosity and density of the dosage form. In general, crystalline polymers have a slower release of drug and longer erosion time. The higher the lactic acid content of the polymer, the slower the drug release and the longer the polymer erosion time. The higher the MW of the polymer, the longer the release and the longer the erosion time. Acid end group polymers will erode faster than aliphatic ester end group polymers.

The polymers and polymer blends must be engineered with the physicochemical properties of the drug in mind, the therapeutic target, the release rate, and the need for timely polymer erosion. The site of implantation is also a key factor. The posterior segment of the eye is particularly sensitive to foreign bodies and chemical insults. A balance of compound physicochemical properties and the polymer properties is required to optimize drug release, polymer erosion, and ocular tolerability. Excessive burst release, long lag times and erosion times that greatly exceed the drug release from the implant must be avoided.

In some embodiments, the bioerodible polyester polymer blend may comprise of at least two polymers. For example, the implant may comprise an acid or ester end group PLA and an acid or ester end group PLGA, wherein at least one of the polymers comprises an ester end group.

In certain embodiments, the bioerodible polyester polymer blend comprises two polymers. In particular embodiments, the ratio of PLA to PLGA may range from between about 10:1 to about 1:10. In other embodiments, the ratio of PLA to PLGA may range from between about 9:1 to about 1:9. In certain other embodiments, the ratio of PLA to PLGA may range from between about 8:1 to about 1:8. In further embodiments, the ratio of PLA to PLGA may range from between about 7:1 to about 1:7. In yet another embodiment, the ratio of PLA to PLGA may range from between about 6:1 to about 1:6. In particular embodiments, the ratio of PLA to PLGA may range from between about 5:1 to about 1:5. In another embodiment, the ratio of PLA to PLGA may range from between about 4:1 to about 1:4.

The PLA polymer of the implant may be selected from polymers with an inherent viscosity selected from between about 0.16 dl/g to about 0.35 dl/g, as measured in 0.1% chloroform (25° C., Ubbelohde) size 0 capillary viscometer.

The PLGA polymer of the implant may be selected from polymers with lactide to glycolide ratios that range from between about 50:50 to about 85:15. The PLGA polymers may have an inherent viscosity ranging from between about 0.16 dl/g to about 1.0 dl/g.

The polyester polymer blend may comprise an ester end group PLGA with a lactide to glycolide ratio that ranges from between about 75:25 and about 85:15 with a viscosity that may be greater than about 0.32 dl/g and an acid or ester end group PLGA with a viscosity that may range from between about 0.16 dl/g and about 1.0 dl/g.

The implant may be fabricated in a number of different ways. For example, the implant may be extruded, injection molded, compression molded, or solvent cast. Various other methods of making or fabricating the implants are also within the scope of this disclosure.

The implant may be introduced, implanted, or delivered into an eye of a subject or patient. For example, the implant may be injected into a vitreous humor of a subject via a self-sealing scleral needle penetration at the pars plana. The needle may be less than about 19 gauge, less than about 20 gauge, less than about 21 gauge, less than about 22 gauge, less than about 25 gauge, or other appropriate diameter. In some embodiments, the needle is a 21 gauge or smaller diameter needle. In certain embodiments, the needle is a small diameter needle, or a needle with a gauge number greater than 21.

The present disclosure also provides methods related to the use of intravitreal implants. In certain embodiments, the present disclosure provides methods of introducing a therapeutic agent into an eye of a subject or a patient. Such methods comprise delivering an implant to as described above into an eye of a subject. In other embodiments, the present disclosure provides methods of treating an ocular disease in a subject that comprise delivering an implant as described above to an eye of the subject. The ocular disease may be selected from at least one of neovascular age related macular degeneration and diabetic macular edema.

The present disclosure also provides for therapeutic agents for use in treating an ocular disease, wherein the therapeutic agent is provided in an implant as described above. Furthermore, the present disclosure provides for use of a therapeutic agent in the manufacture of an implant as described above for treatment of a subject in need thereof. The present disclosure also provides a pre-loaded injector assembly comprising a needle and an implant as described above.

Examples

To further illustrate these embodiments, the following examples are provided. These examples are not intended to limit the scope of the claimed invention, which should be determined solely on the basis of the attached claims.

The desired release rate of axitinib from an intraocular implant was determined from the $IC_{50}$ of the compound. It is assumed that an intravitreal implant must deliver a therapeutic concentration in the vitreous at least 100 fold higher than its $IC_{50}$ to be effective. This allows for a diffusion gradient to be established across the posterior segment of the eye. This diffusional gradient can sometimes result in a 10 fold drop in vitreous drug concentration from an implant to the retina. An additional 10 fold level above the $10 \times IC_{50}$ is required to accommodate penetration across the retinal pigment epithelium RPE and into the affected cells as tyrosine kinases are intracellular targets. Hence, the target vitreous concentration was estimated to be 100× the cellular $IC_{50}$ of the compound.

The drug must also have sufficient solubility to support a diffusional release from the implant into the vitreous. Compounds diffuse against a concentration gradient. If the concentration in the vitreous equals the solubility of the compound, there is no driving force for diffusion and release from the implant will be stopped.

Based on this, it is anticipated that a vitreous concentration of 7.7 ng/mL is needed for axitinib. The solubility supports this allowing for diffusion from the implant. Assuming a vitreous half-life for axitinib of two hours, 256 ng/day would be needed for efficacy for a 4 mL volume. Many TKIs do not have a solubility/potency ratio that supports establishing the required concentration gradients. Pazopanib, for example, can only achieve a concentration of 10× its $IC_{50}$ as seen in Table 1.

TABLE 1

Select TKI required release rates for intravitreal administration.

| Compound | IC50/EC50 | 100× = Cvit | Aq. Sol | Release rate |
|---|---|---|---|---|
| Axitinib | 0.2 nM | 7.7 ng/mL | 0.2 ug/mL | 256 ng/day |
| Pazopanib | 30 nM | 1.3 ug/mL | 3.3 ug/mL | 32 μg/day |

A design of experiments was set up to identify the design space for the axitinib formulations. Different PLA and PLGA polymers whose characteristics are given in Table 2 were used to formulate the axitinib implants according to the matrix in a table of FIG. 1B where weights of polymers are given in mg. These included the Evonik Resomers R202S and R203S (high and low MW PLA, ester end group), RG502 and RG503 (high and low MW 50:50 PLA:PGA copolymer, ester end group), RG752H (acid end group 75:25 PLA:PGA copolymer) and RG756S (high MW, ester end group 75:25 PLGA). The polymers were chosen to evaluate the effects of MW, co-monomer ratio, and end group on drug release and polymer erosion as depicted in FIG. 1. The chart in FIG. 1 describes various polymer matrixes of PLA and PLGA. The higher the molecular weight of the PLA and PLGA, the release duration increased and the matrix degradation increased. The different shading in the chart refers to release duration, a 1-3 month release duration, a 3-12 month duration, or a greater than 12 month duration.

TABLE 2

Characteristics of PLA polymers and PLGA polymers.

| Polymer Type | Inherent viscosity (dl/g) | Molecular Weight (kDa) | Glass Transition Temperature (° C.) | Ester End or Acid End | PLA or PLGA (lactide to glycolide ratio) |
|---|---|---|---|---|---|
| R203S | 0.25-0.35 | 18-28 | 46-50 | Ester End | PLA |
| R202S | 0.16-0.24 | 10-18 | 38-42 | Ester End | PLA |
| RG756S | 0.71-1.0 | 76-115 | 49-55 | Ester End | PLGA 75:25 |
| RG752H | 0.14-0.22 | 4-15 | 42-46 | Acid End | PLGA 75:25 |
| RG503 | 0.32-0.44 | 24-38 | 44-48 | Ester End | PLGA 50:50 |
| RG502 | 0.16-0.24 | 7-17 | 42-46 | Ester End | PLGA 50:50 |
| RG753S | 0.32-0.44 | | | | PLGA 75:25 |
| RG505 | 0.61-0.74 | 54-69 | 48-52 | Ester End | PLGA 50:50 |

The formulations were manufactured by first milling the axitinib drug substance and the PLA and PLGA polymers using a jet mill. This allowed for consistent particle size reduction of the starting materials. The polymers were then mixed with axitinib according to the matrix in the table of FIG. 1B. Each mixture was then heated above its glass transition temperature to form a viscous dough. The dough was mixed to achieve a homogeneous dispersion of axitinib in the blend. Once mixed, the dough was heat compressed on a specially designed press. The heat pressed axitinib/PLGA wafers were then cut into individual implants.

Release of the axitinib from the implants was assessed in vitro. Implants were placed into 50 mL polypropylene vials containing 45 mL of isotonic saline at pH 7.4 as the release media. The vials were then placed on a shaker bath to agitate the medium at 37° C. At pre-determined timepoints the media was sampled and the entire receiver media was replaced with fresh saline. The axitinib concentration in the sampled aliquot was quantified by High Performance Liquid Chromatography (HPLC) using a Waters Alliance e2695 system with a C-18 Hypersil ODS column. The axitinib concentrations were used to define the cumulative in vitro release of axitinib from the implant as well as the daily axitinib release rate.

A summary of the release results for formulations 1 through 10 with a 60% axitinib load in the design matrix from the table of FIG. 1B is provided below. The 40% loaded axitinib implants released similarly to their 60% counterparts. Representative release profiles are depicted in FIGS. 2A through 5B. In summary, all implants manufactured with a single PLGA polymer except 756S erode within nine to 12 weeks and are not suitable for a six-month implant. Implants manufactured with a single PLA polymer or the 756S polymer released at sub-therapeutic rates and may not bioerode for years. However, axitinib implants manufactured from specific blends of a PLA and a PLGA demonstrated promising release profiles.

Formulation 1: (R202S; PLA) 60% axitinib load, 1% burst release then 3% released over 14 weeks. The release rate was marginally therapeutic at 60 days.

Formulation 2: (R203S; PLA) 60% axitinib load, 1.5% burst then 3% released over 14 weeks. The release rate was sub-therapeutic after the burst out to 13 weeks.

Formulations 3-5: (RG502, RG503, RG752H; PLGAs) 60% axitinib load, 5% was released in eight weeks, but the implants fall apart between nine and 12 weeks.

Formulation 6: (RG756S; high MW PLGA) 60% axitinib load, sub-therapeutic release rate after initial burst for 11 weeks. 11 to 13 weeks therapeutic. 3.5% at 14 weeks.

Formulation 7: (R203S:RG756S) 60% axitinib load. Linear release, but only 2% released over 13 weeks.

Formulation 8: (R202S:RG756S) 60% axitinib load. Lag for three weeks then therapeutic. 6% released over 13 weeks.

Formulation 9: (R203S:RG503) 40% axitinib load. 6% over 20 weeks, four-week lag then therapeutic release rate achieved.

Formulation 10: (R203S:RG752H) 60% axitinib load. 5% over 13 weeks. No lag and marginally therapeutic release rate out to four weeks.

Figure 2A:
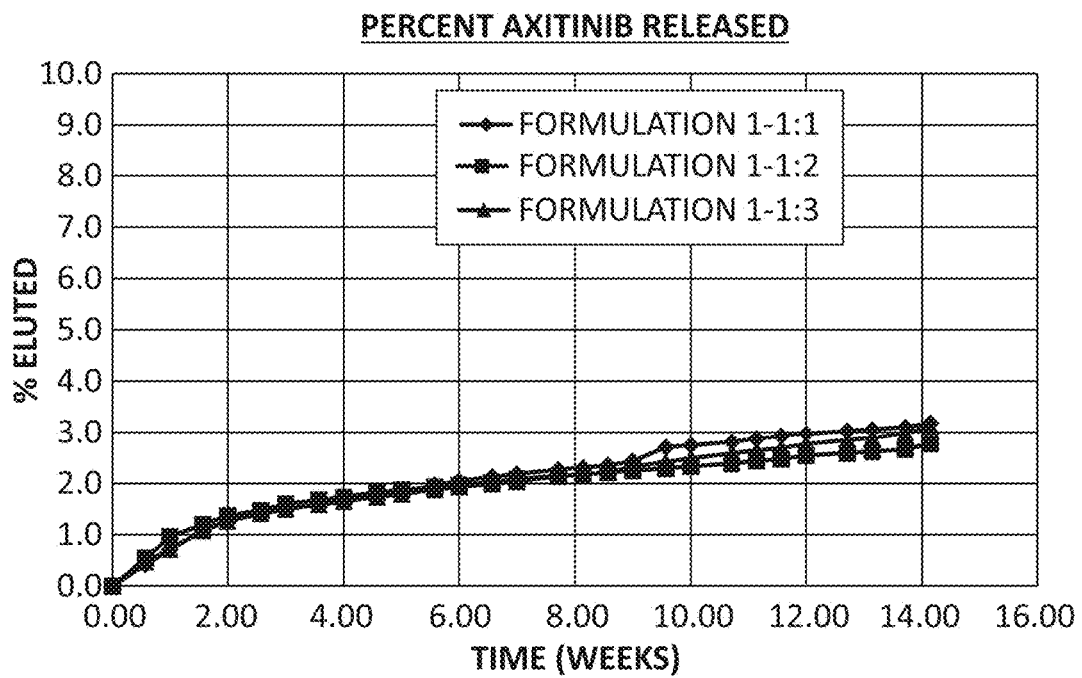
FIGS. 2A and 2B are graphs of axitinib cumulative and daily in vitro release from a first formulation, according to one embodiment.
Figure 2B:
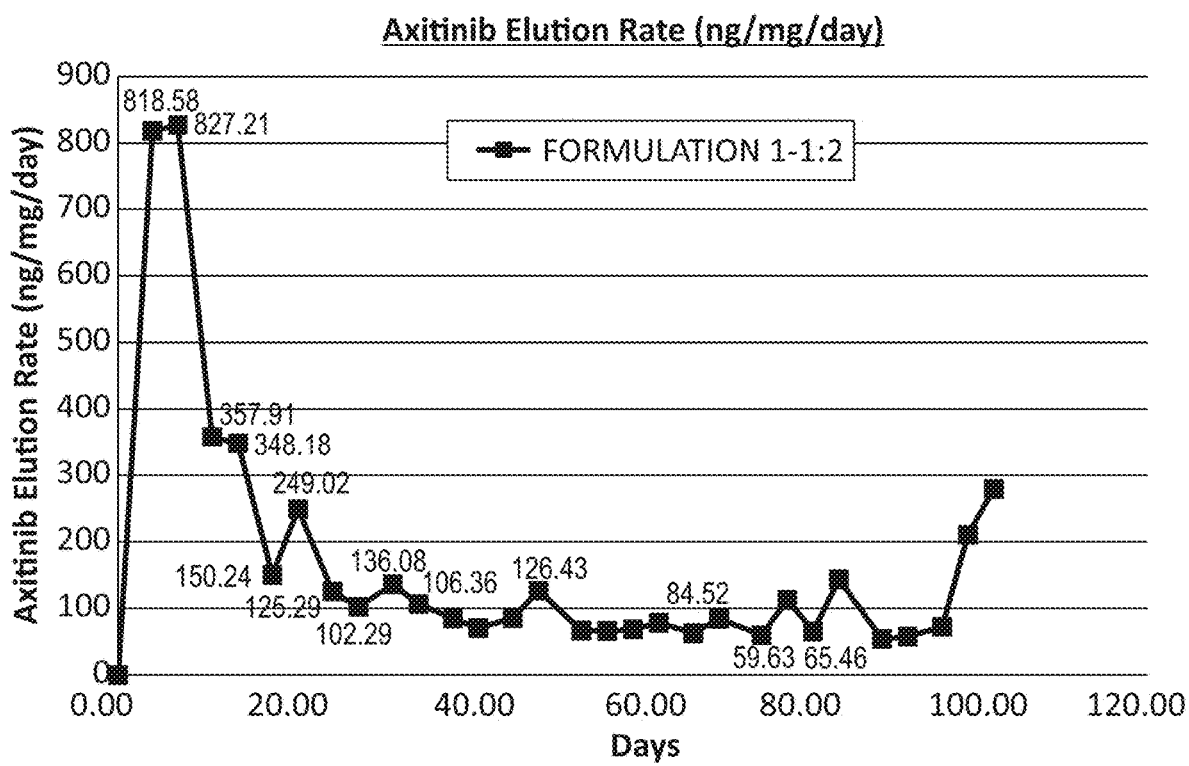

FIGS. 2A and 2B are graphs of axitinib cumulative and daily in vitro release from the first formulation. FIG. 2A illustrates the percent eluted over time (for three samples) and FIG. 2B illustrates the elution rate in ng/mg/day (of one sample).

Figure 3A:
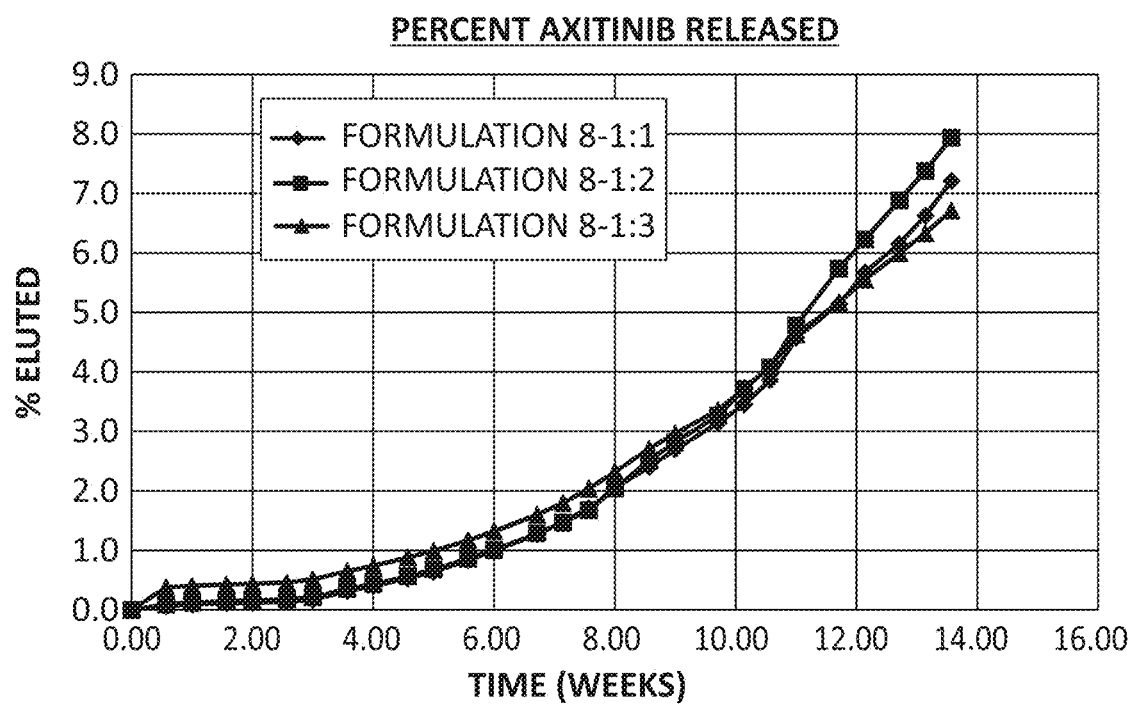
FIGS. 3A and 3B are graphs of axitinib cumulative and daily in vitro release from an eighth formulation, according to one embodiment.
Figure 3B:
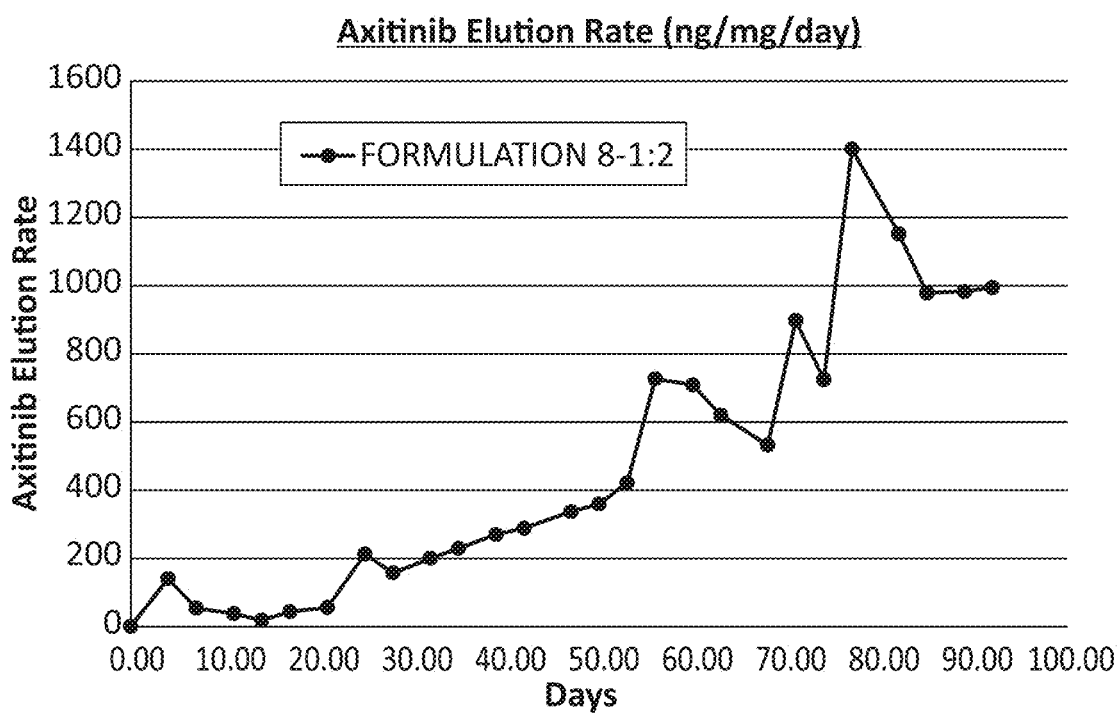

FIGS. 3A and 3B are graphs of axitinib cumulative and daily in vitro release from the eighth formulation. FIG. 3A illustrates the percent eluted over time (for three samples) and FIG. 3B illustrates the elution rate in ng/mg/day (of one sample).

Figure 4A:
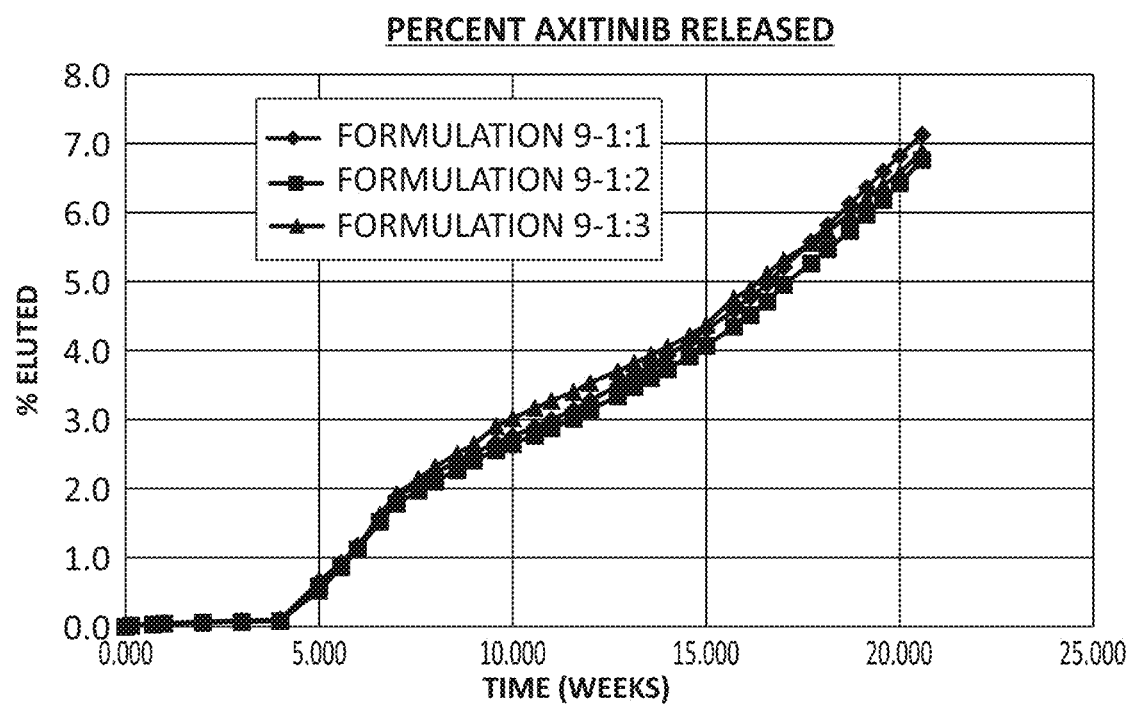
FIGS. 4A and 4B are graphs of axitinib cumulative and daily in vitro release from a ninth formulation, according to one embodiment.
Figure 4B:
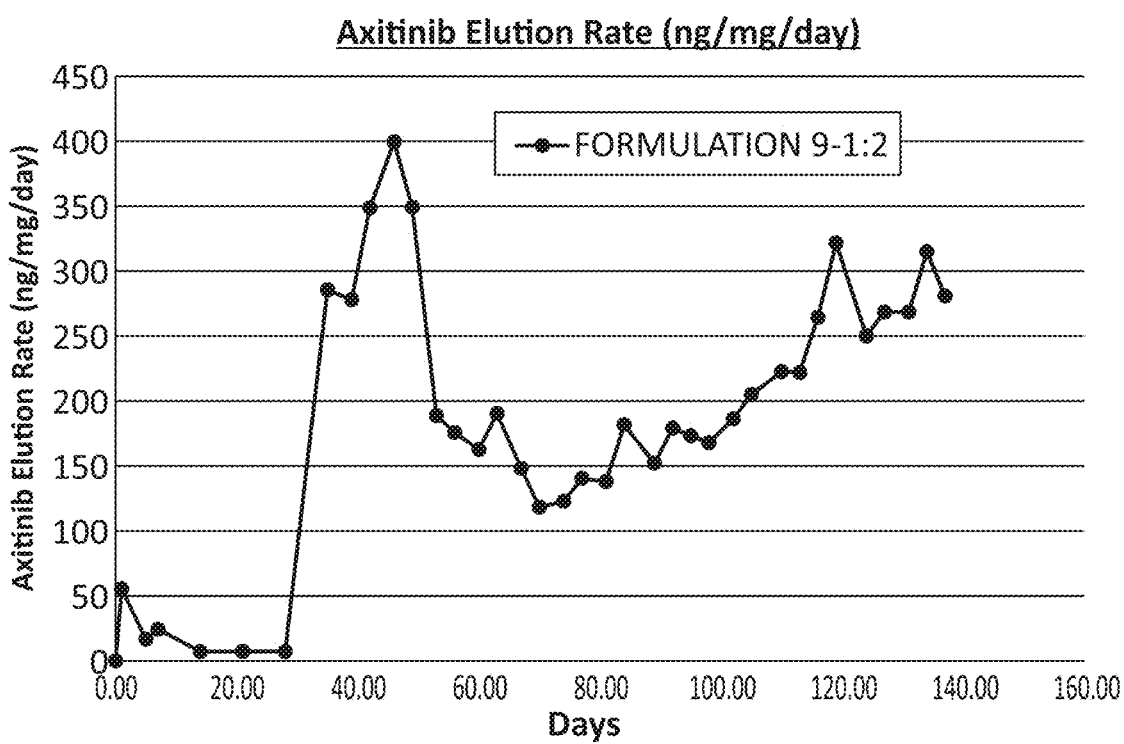

FIGS. 4A and 4B are graphs of axitinib cumulative and daily in vitro release from the ninth formulation. FIG. 4A illustrates the percent eluted over time (for three samples) and FIG. 4B illustrates the elution rate in ng/mg/day (of one sample).

Figure 5A:
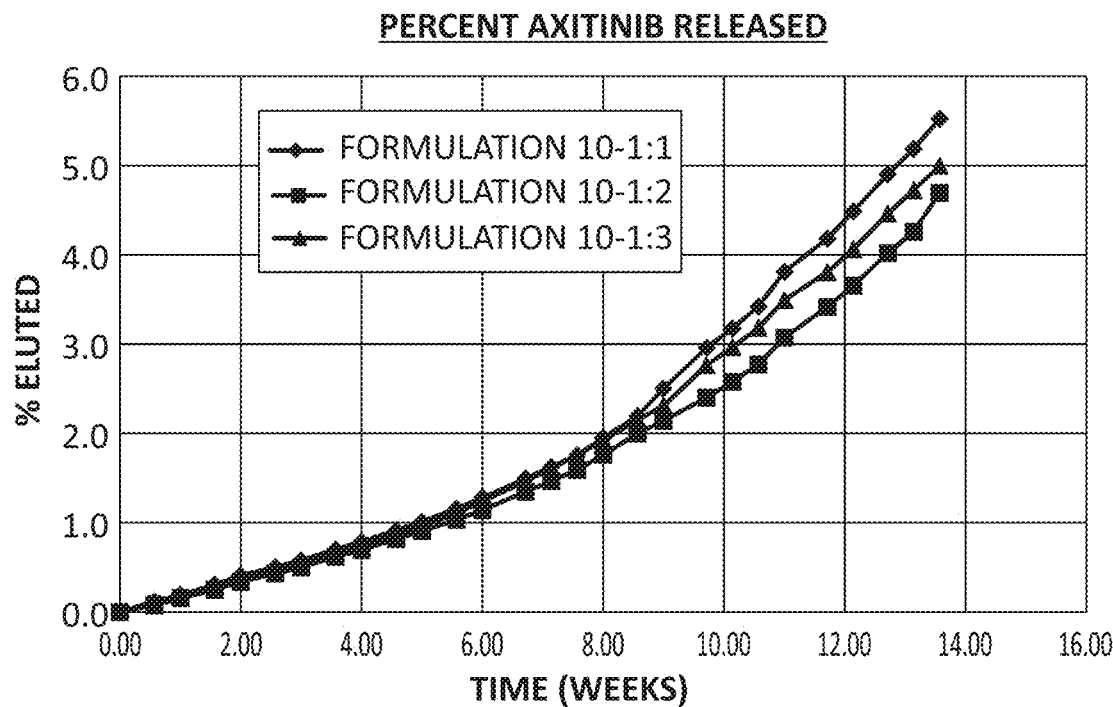
FIGS. 5A and 5B are graphs of axitinib cumulative and daily in vitro release from a tenth formulation, according to one embodiment.
Figure 5B:
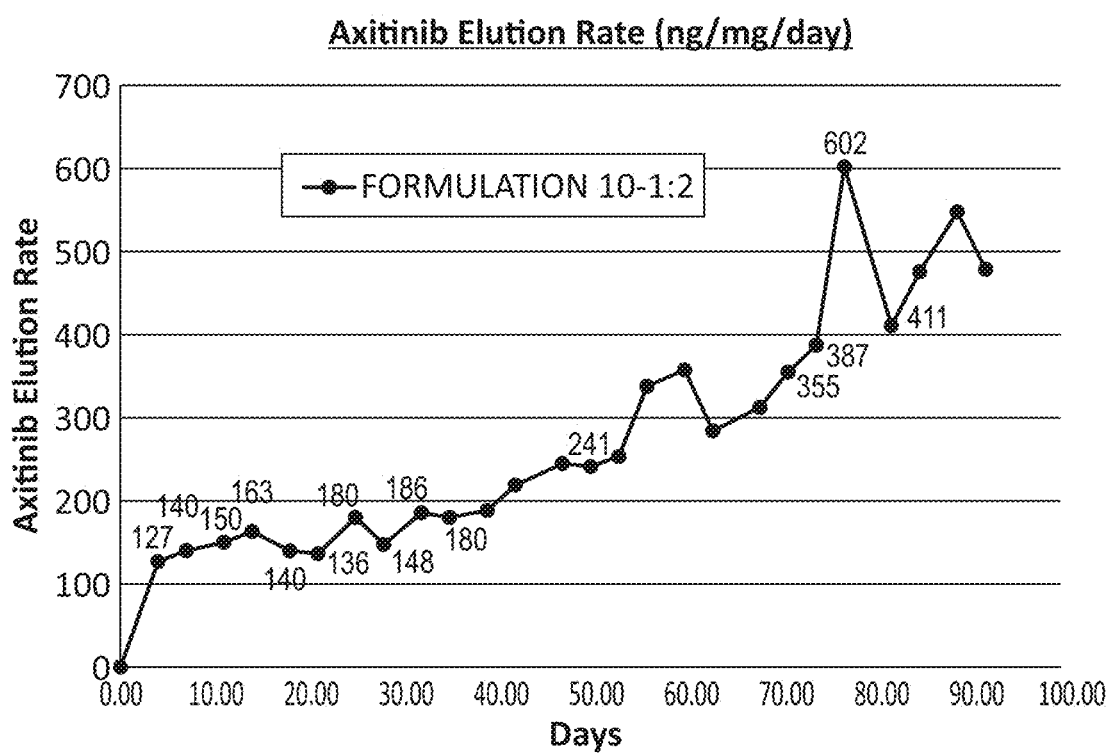

FIGS. 5A and 5B are graphs of axitinib cumulative and daily in vitro release from the tenth formulation. FIG. 5A illustrates the percent eluted over time (for three samples) and FIG. 5B illustrates the elution rate in ng/mg/day (of one sample).

Figure 6:
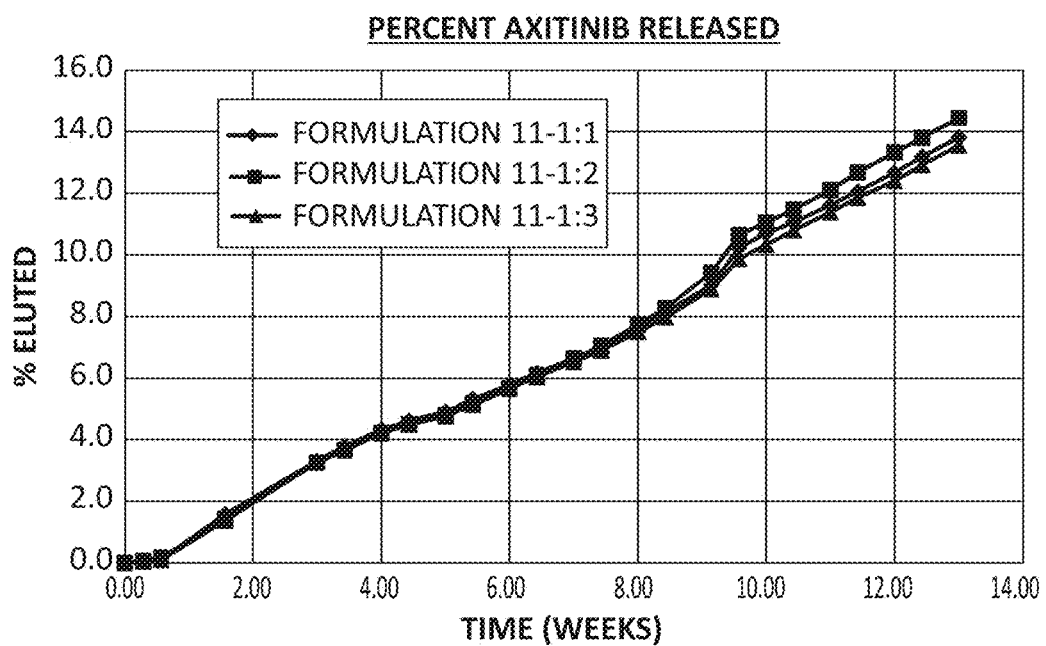
FIG. 6 is a graph from a 60% axitinib-loaded polymer blend, according to one embodiment.

Implant formulations comprising blends of PLA and PLGA were chosen for optimization. Specifically, the following blends were evaluated: R203S:RG752H and R202S:RG503. For each blend, the ratio of PLA to PLGA was varied from 1:1 to 1:2 and 1:3, with increasing PLGA content. Implants containing 60% axitinib were manufactured with the polymer blends by hot melt compression as described above. The release of axitinib was determined as described above. The optimization yielded formulations that display a linear release with minimal burst or lag time and meet the release criteria and are expected to erode in a timely fashion. The release profile of an exemplary sample is depicted in FIG. 6 (three samples of R202S:RG503, PLA to PLGA ratio 1:3, 60% axitinib load).

A three month intravitreal tolerability study with axitinib/PLGA was conducted in Dutch Belted (DB) and New Zealand White rabbits. Axitinib-loaded and placebo implants were well-tolerated out to day 90 based on ophthalmic examination.

Figure 7:
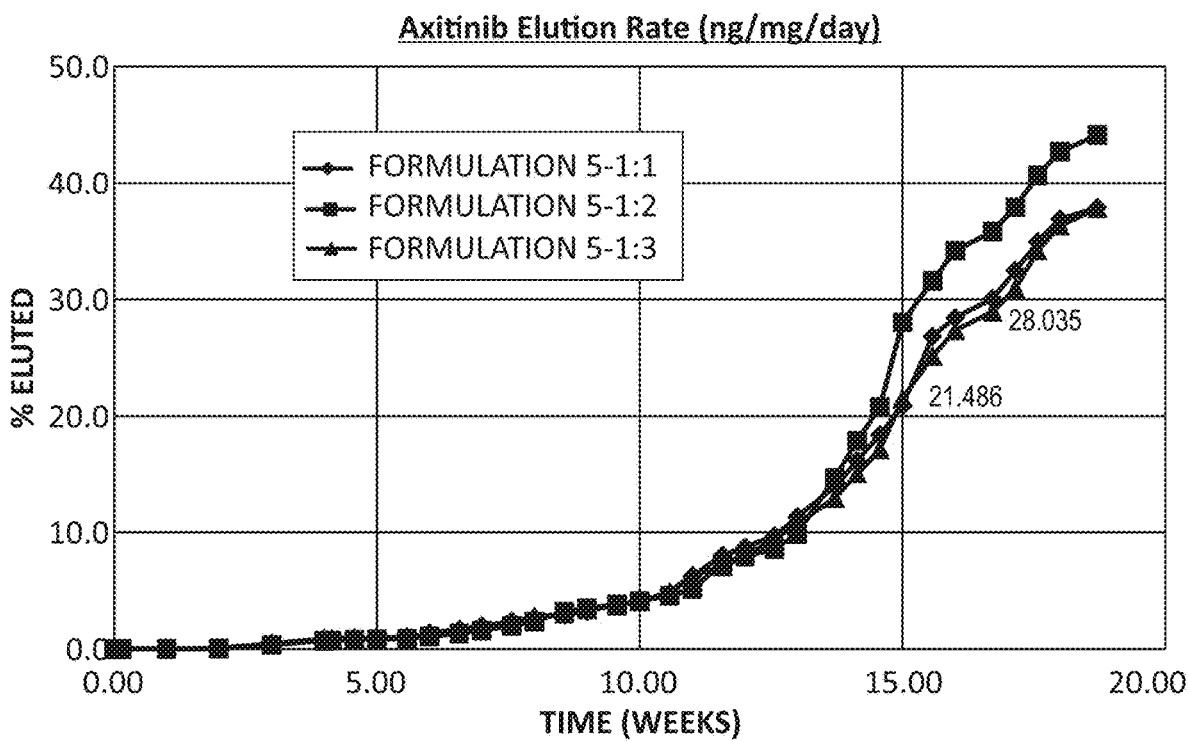
FIG. 7 is a graph from a 60% axitinib-loaded polymer blend according to a fifth formulation, according to one embodiment.

Formulation 5 from the original design of experiments was chosen for the tolerability and efficacy studies. The slowly increasing rate of axitinib release from Formulation 5 enabled the tolerability and efficacy as a function of release rate to be determined. The in vitro release of axitinib from formulation 5 (RG752H) is shown in FIG. 7 (for three samples).

Figure 8:
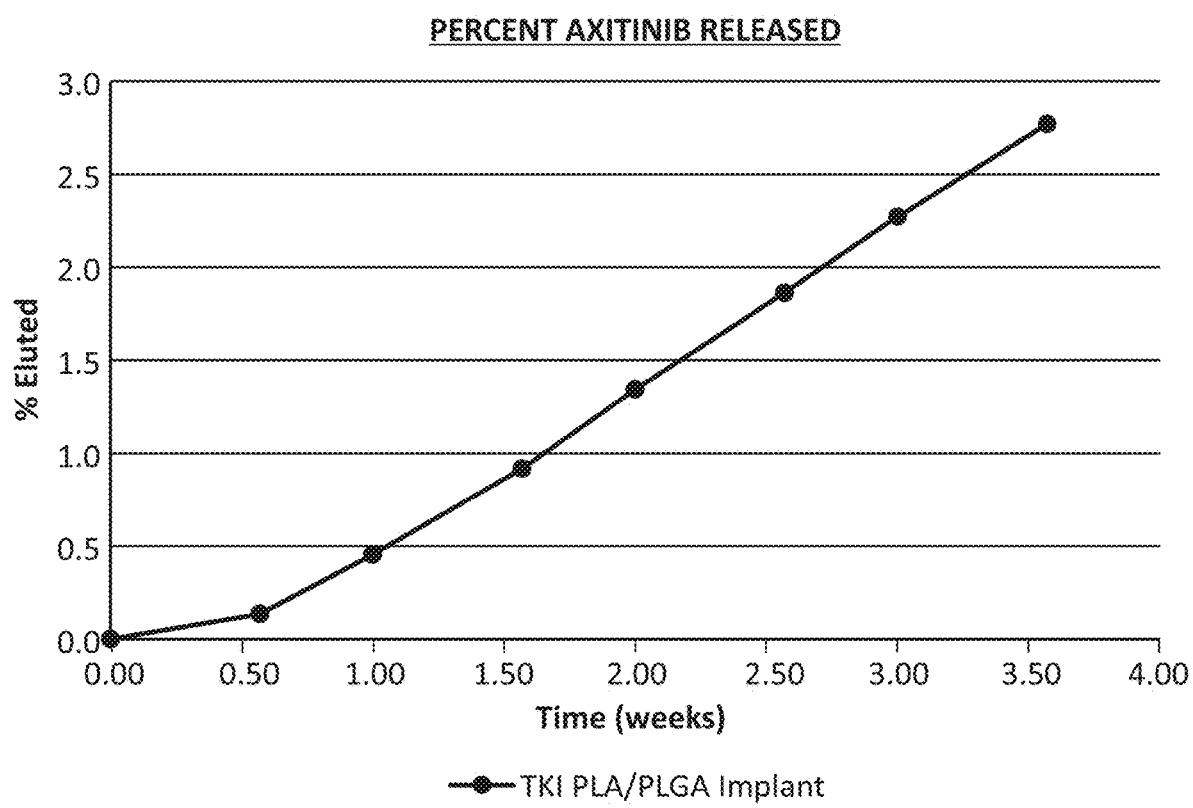
FIG. 8 is a graph of a release profile of TKI from a PLA/PLGA implant over a four week period.

FIG. 8 illustrates a mean release profile of TKI from an optimized PLA/PLGA implant over a period of four weeks (three samples of R202S:RG503, PLA to PLGA ratio 1:3, 60% axitinib load). The burst release of the TKI is less than 1% after an initial 24-hour period after implantation. In fact, the percent release of TKI is less than 1% after a week and a half post-implantation.

Figure 9A:
FIG. 9A is a picture of an axitinib implant in the vitreous of a Dutch Belted rabbit initially after implant.
Figure 9B:
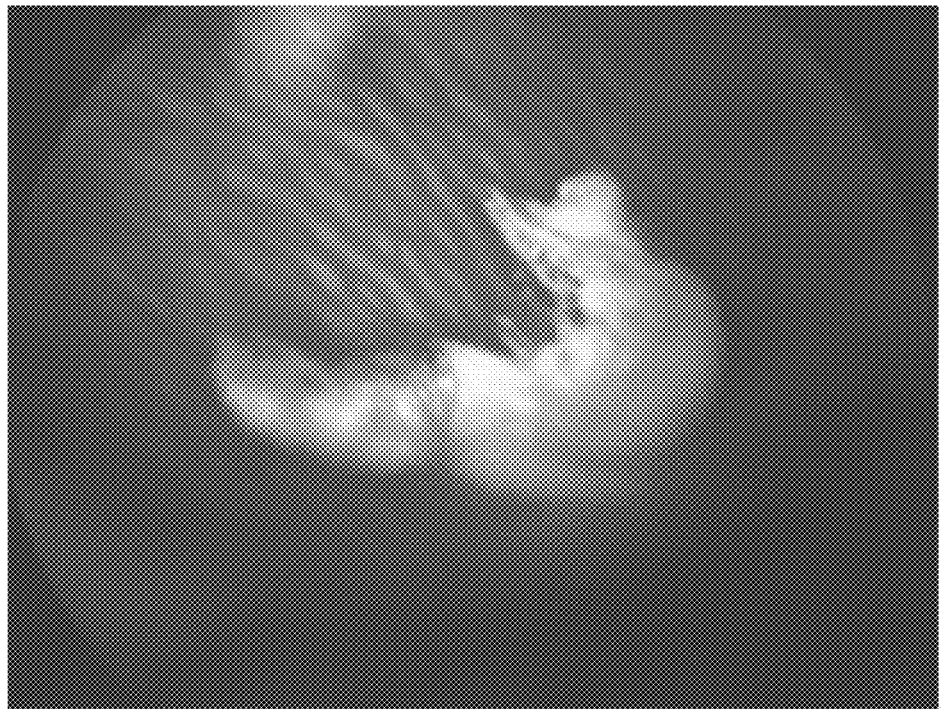
FIG. 9B is a picture of an axitinib-loaded implant in the vitreous of a Dutch Belted rabbit 50 days after implant.

Formulation 5 displays no lag time, rapidly approaches the anticipated effective axitinib release rate of 256 ng/day, and slowly increases the release rate. Furthermore, the implant begins to degrade in vitro at about 12 weeks with softening occurring around 10 weeks. FIG. 9A depicts the implant in the eye of a DB rabbit initially, and FIG. 9B depicts the implantation 60 days after implantation. This shows clear hydration and the beginnings of implant erosion at day 60. Hence, the in vitro erosion rate correlated well with the in vivo erosion rate.

Axitinib intravitreal implants were evaluated in a translation model of persistent retinal vessel leakage following a single intravitreal injection. The model is created by injecting DL-alpha-aminoadipic acid into the vitreous of DB rabbits. The model produces a persistent retinal vascular leakage that responds to anti-VEGF treatment. Retinal leakage is monitored by fluorescein angiography. The model was validated using a 2-mg injection of the commercial Eylea® (aflibercept) product. Eylea® (aflibercept) reduced the "leakage score" by 10 to 20 from baseline and lasted approximately two months as expected, matching the clinical performance. One axitinib implant inhibited fluorescein angiography leakage similar to Eylea® (aflibercept) for up to 115 days. The placebo had no effect on the leakage score.

Figure 10:
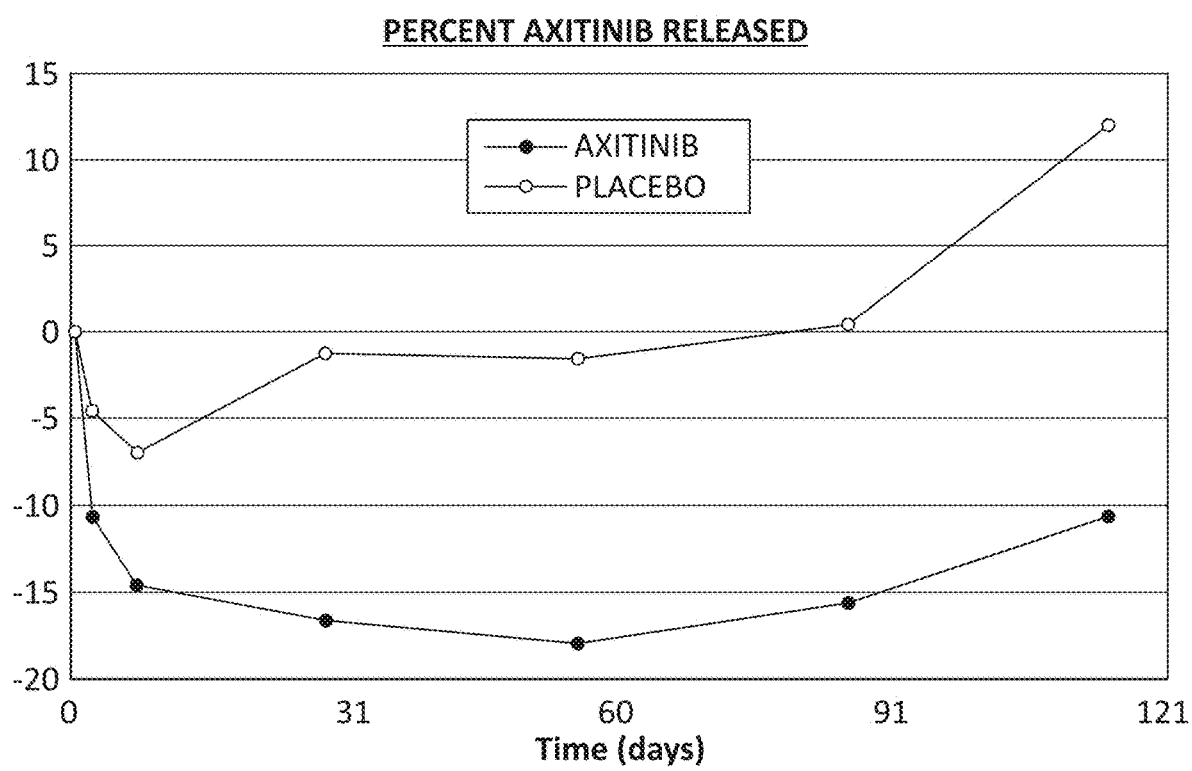
FIG. 10 is a graph of the efficacy of an axitinib-loaded implant in preventing leakage assessed by fluorescein angiography in the DL-AAA model of persistent retinal vascular leakage (1 Formulation 5 axitinib implant=1 a-AXT and 1 placebo implant=1b-TMCPlac). The y-axis represents a leakage score based on a predefined scale.
Figure 11A:
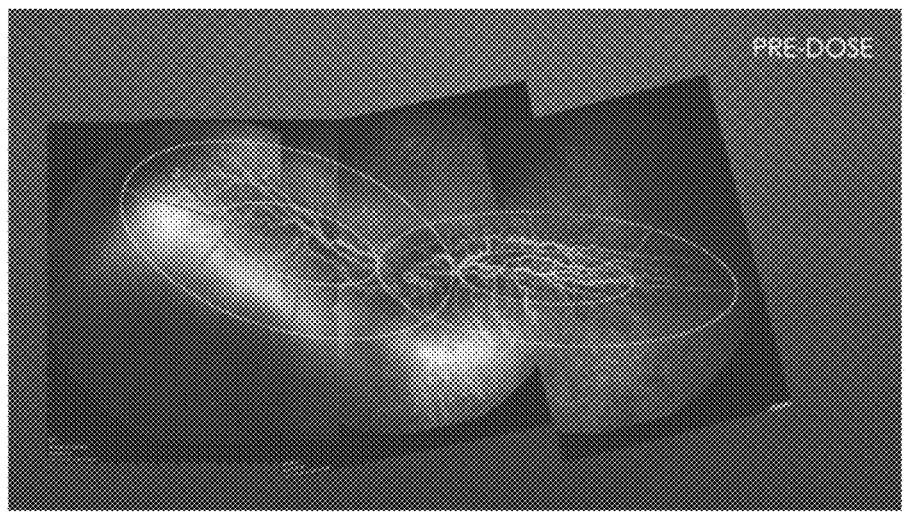
FIG. 11A is a fluorescein angiography of an axitinib implant before implantation.
Figure 11B:
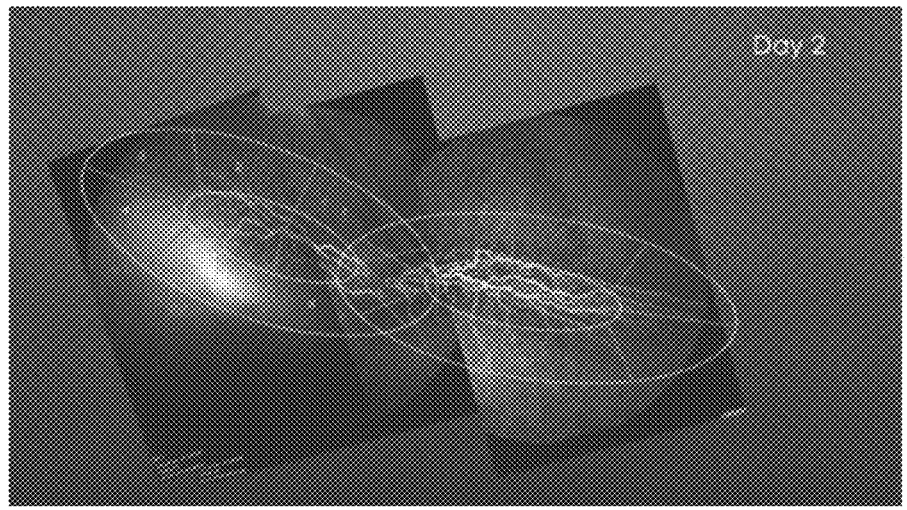
FIG. 11B is a fluorescein angiography of an axitinib implant two days post-implantation.
Figure 11C:
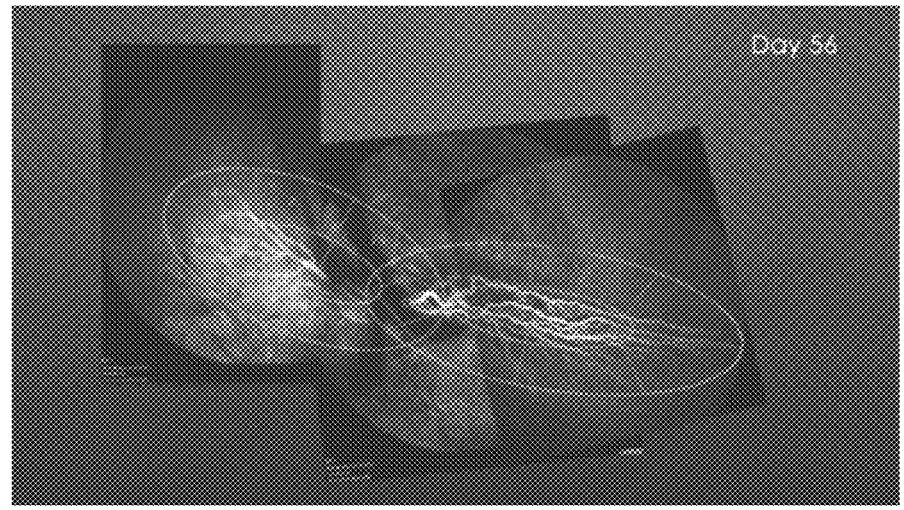
FIG. 11C is a fluorescein angiography of an axitinib implant 56 days post-implantation.
Figure 11D:
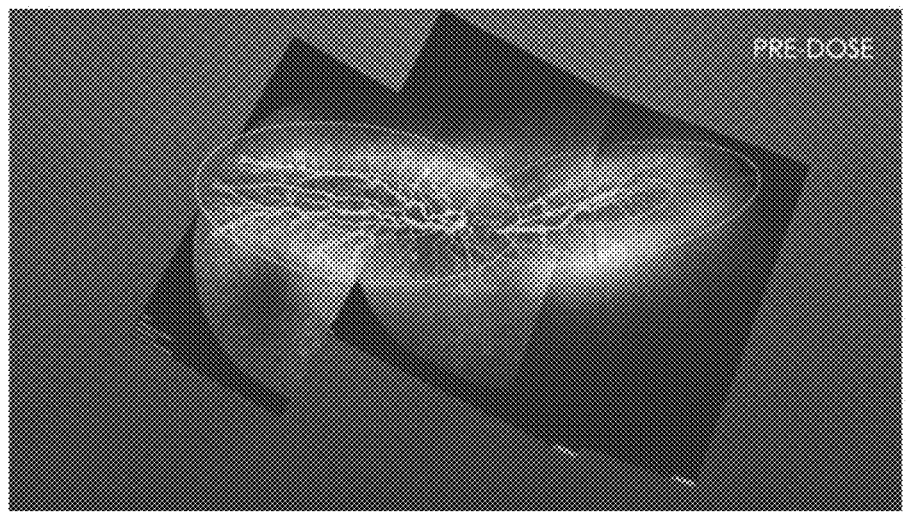
FIG. 11D is a fluorescein angiography of a placebo-loaded implant before implantation.
Figure 11E:
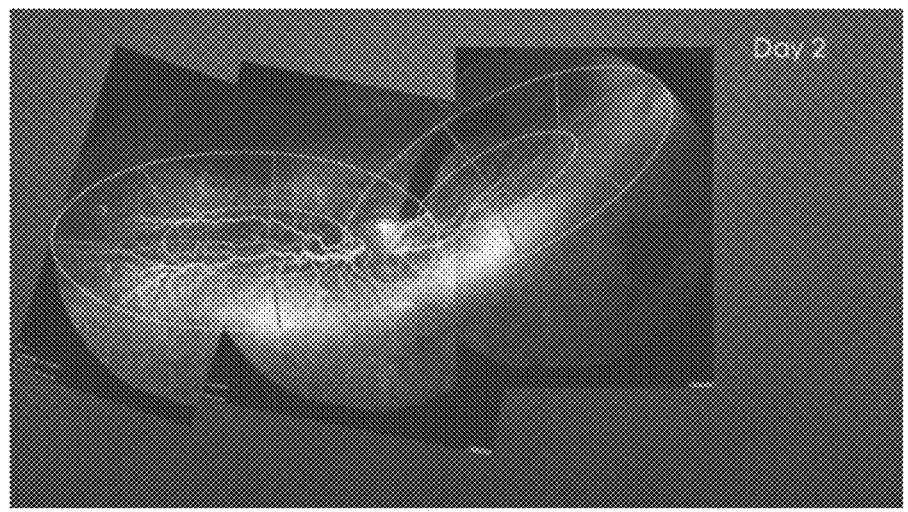
FIG. 11E is a fluorescein angiography of a placebo-loaded implant two days post-implantation.
Figure 11F:
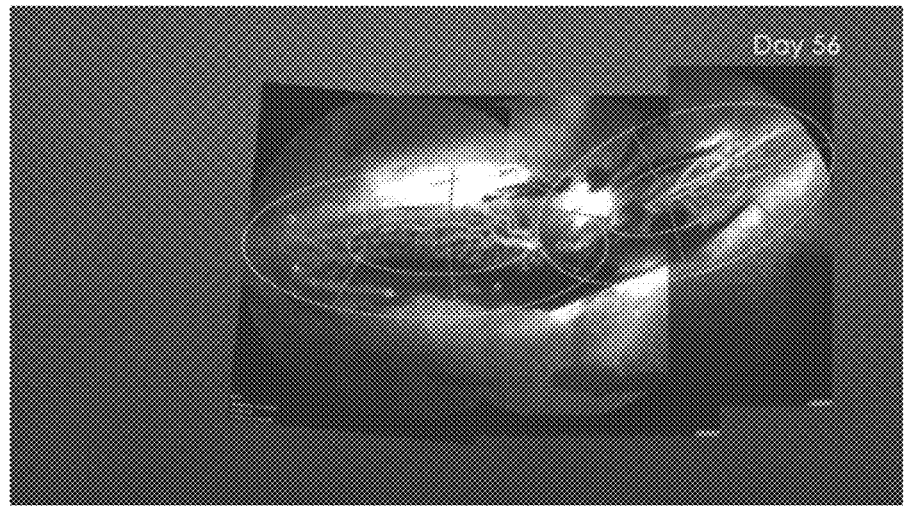
FIG. 11F is a fluorescein angiography of a placebo-loaded implant 56 days post-implantation.

FIG. 10 depicts the leakage scores normalize to baseline values of axitinib compared to a placebo. FIGS. 11A-11C show the fluorescein angiography of the axitinib implant at before implantation, two days after implantation, and 56 days after implantation. FIGS. 11D-11F show the fluorescein angiography of the placebo implant before implantation, two days after implantation, and 56 days after implantation.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. An implant comprising:
   axitinib; and
   a bioerodible polyester polymer blend comprising at least two polymers, wherein the bioerodible polyester polymer blend comprises an acid or ester end group polylactic acid (PLA) and an acid or ester end group poly-D,L-lactide-co-glycolide (PLGA), and wherein at least one of the two polymers comprises an ester end group,
   wherein the PLA is selected from polymers with an inherent viscosity selected from between about 0.16 dl/g to about 0.35 dl/g as measured in 0.1% chloroform (25° C., Ubbelohde) size 0 capillary viscometer, and
   wherein the axitinib is present in the implant in an amount selected from a range of between about 5 and about 80 percent (w/w).

2. The implant of claim 1, wherein the axitinib is present in the implant in an amount selected from a range of between about 40 to about 80 percent (w/w).

3. An implant comprising:
axitinib; and
a bioerodible polyester polymer blend comprising at least two polymers, wherein the bioerodible polyester polymer blend comprises an acid or ester end group polylactic acid (PLA) and an acid or ester end group poly-D,L-lactide-co-glycolide (PLGA), and wherein at least one of the two polymers comprises an ester end group,
wherein the PLGA is selected from polymers with lactide to glycolide ratios selected from between about 50:50 to about 85:15, and wherein the PLGA is selected from polymers with an inherent viscosity selected from between about 0.16 dl/g to about 1.0 dl/g, and
wherein the axitinib is present in the implant in an amount selected from a range of between about 5 and about 80 percent (w/w).

4. An implant comprising:
axitinib, and
a bioerodible polyester polymer blend, comprising an ester end group poly-D,L-lactide-co-glycolide (PLGA) with a 75:25 or 85:15 lactide to glycolide ratio and an inherent viscosity of greater than about 0.32 dl/g and an acid or ester end group PLGA with an inherent viscosity selected from between about 0.16 dl/g to about 1.0 dl/g,
wherein the axitinib is present in the implant in an amount selected from a range of between about 5 and about 80 percent (w/w).

5. An implant comprising:
axitinib, and
a bioerodible polyster polymer blend, comprising at least two polymers, wherein the bioerodible polyester polymer blend comprises an acid or ester end group polylactic acid (PLA) and an acid or ester end group poly-D,L-lactide-co-glycolide (PLGA), and wherein at least one of the two polymers comprises an ester end group,
wherein the ratio of PLA to PLGA is selected from a range of between about 10:1 to about 1:10, a range of between about 9:1 to about 1:9, a range of between about 8:1 to about 1:8, a range of between about 7:1 to about 1:7, a range of between about 6:1 to about 1:6, a range of between about 5:1 to about 1:5, or a range of between about 4:1 to about 1:4 and
wherein the axitinib is present in the implant in an amount selected from a range of between about 5 and about 80 percent (w/w).

6. The implant of claim 5, wherein the ratio of PLA to PLGA is selected from a range of between about 4:1 to about 1:4.

7. An implant comprising:
axitinib, and
a bioerodible polyester polymer blend,
wherein the axitinib is present in the implant in an amount selected from a range of between about 5 and 80 percent (w/w), and
wherein the release rate of the axitinib from the composite implant is selected from a range of between about 10 ng/day to about 10 mg/day.

8. The implant of claim 1, wherein the implant releases the axitinib for at least six months from implantation in a vitreous humor of an eye of a subject.

9. The implant of claim 1, wherein the implant releases the axitinib for at least one year from implantation in a vitreous humor of an eye of a subject.

10. An implant comprising:
axitinib, and
a bioerodible polyester polymer blend,
wherein the axitinib is present in the implant in an amount selected from a range of between about 5 and 80 percent (w/w), and
wherein a burst release of axitinib from the implant is less than 10 percent (w/w) over an initial 24-hour period from implantation in an eye of a subject.

11. An implant comprising:
axitinib, and
a bioerodible polyester polymer blend,
wherein the axitinib is present in the implant in an amount selected from a range of between about 5 and 80 percent (w/w), and
wherein a burst release of the axitinib from the implant is less than 1 percent (w/w) over an initial 24-hour period from implantation in an eye of a subject.

12. An implant comprising:
axitinib, and
a bioerodible polyester polymer blend,
wherein the axitinib is present in the implant in an amount selected from a range of between about 5 and 80 percent (w/w), and
wherein the release rate of the axitinib from the implant is substantially constant over an initial three-month period from implantation beginning with the end of the burst release or lag phase, but not more than 14 days post-implantation.

13. An implant comprising:
axitinib, and
a bioerodible polyester polymer blend,
wherein the axitinib is present in the implant in an amount selected from a range of between about 5 and 80 percent (w/w), and
wherein the release rate of the axitinib from the implant is near-zero order or pseudo-zero order over an initial three-month period from implantation beginning with the end of the burst release or lag phase, but not more than 14 days post-implantation.

* * * * *